(12) United States Patent
Rosell Ferrer et al.

(10) Patent No.: US 8,808,190 B2
(45) Date of Patent: Aug. 19, 2014

(54) PLANAR COIL ARRANGEMENT FOR A MAGNETIC INDUCTION IMPEDANCE MEASUREMENT APPARATUS

(75) Inventors: Francisco Javier Rosell Ferrer, Barcelona (ES); Claudia Hannelore Igney, Erlangen (DE); Matthias Hamsch, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 13/981,624

(22) PCT Filed: Feb. 1, 2012

(86) PCT No.: PCT/IB2012/050469
§ 371 (c)(1),
(2), (4) Date: Jul. 25, 2013

(87) PCT Pub. No.: WO2012/104799
PCT Pub. Date: Aug. 9, 2012

(65) Prior Publication Data
US 2013/0303924 A1 Nov. 14, 2013

(30) Foreign Application Priority Data
Feb. 3, 2011 (EP) .................................. 11153167

(51) Int. Cl.
*A61B 5/02* (2006.01)
(52) U.S. Cl.
USPC ........................................................ 600/508
(58) Field of Classification Search
USPC ............................................... 600/508, 547
See application file for complete search history.

(56) References Cited

U.S. PATENT DOCUMENTS

| | | | |
|---|---|---|---|
| 4,613,817 | A | 9/1986 | Hoenig |
| 7,164,941 | B2 | 1/2007 | Misczynski et al. |
| 7,196,629 | B2 | 3/2007 | Ruoss et al. |
| 7,740,588 | B1 | 6/2010 | Sciarra |
| 2007/0115120 | A1 | 5/2007 | Ito et al. |
| 2008/0106421 | A1 | 5/2008 | Adams et al. |
| 2010/0222686 | A1 | 9/2010 | Fisher et al. |

FOREIGN PATENT DOCUMENTS

| | | |
|---|---|---|
| WO | 8905115 A1 | 6/1989 |
| WO | 2008018018 A2 | 2/2008 |

OTHER PUBLICATIONS

Akram Alomainy et al, "Numerical and Experimental Evaluation of a Compact Sensor Antenna for Healthcare Devices", IEEE Transactions on Biomedical Circuits and Systems, vol. 1, No. 4, Dec. 2007, pp. 242-249.

Watson S. et al, "A comparison of sensors for minimizing the primary signal in planar-array magnetic induction tomography; Comparison of sensors for minimizing the primary signal in planar-array MIT", Physiological Measurement, Institute of Physics Publishing, Bristol, GB, vol. 26, No. 2, Apr. 1, 2005, pp. S319-S331, XP020092171, ISSN: 0967-3334.

*Primary Examiner* — Robert N Wieland

(57) ABSTRACT

A planar coil arrangement (400) for a magnetic induction impedance measurement apparatus comprises an excitation coil (102) configured for generating a magnetic excitation field in an object, and a detection coil (404) configured for detecting a magnetic response field generated in response to the magnetic excitation field inducing a current in the object. In order to minimize an effect of the magnetic excitation field in the detection coil (404), the detection coil (404) is radially symmetrical shaped with respect to the excitation coil (102) and is arranged relative to the excitation coil (102) such that the magnetic excitation field is minimized in the detection coil (404).

14 Claims, 3 Drawing Sheets

PLANAR COIL ARRANGEMENT FOR A MAGNETIC INDUCTION IMPEDANCE MEASUREMENT APPARATUS

FIELD OF THE INVENTION

The invention relates to the field of magnetic induction impedance measurement technique, and particularly to a planar coil arrangement for a magnetic induction impedance measurement apparatus, a magnetic induction impedance measurement apparatus for determining a physiological parameter of a person, and a method of determining a physiological parameter of a person.

BACKGROUND OF THE INVENTION

A magnetic induction impedance measurement (MIT) technique is usable, for example, in clinical applications, in order to determine a physiological parameter of a person. This contactless examining technique is based on measuring a signal indicative of an electrical conductivity of a tissue of the person to be examined. To this end, a respective coil arrangement for a magnetic induction impedance measurement apparatus comprises an excitation coil and a detection coil. In operation of the magnetic induction impedance measurement apparatus, a time-varying current is induced in the excitation coil such that the excitation coil generates a magnetic excitation field which penetrates through the tissue to be examined and accordingly induces an eddy current within the electrically conductive tissue of the person to be examined. The magnitude of the eddy current is based on the magnetic flux density and the connectivity of the tissue. A magnetic response field is generated by the eddy current and is detected by the detection coil in that a current or a voltage is induced in the detection coil. The current or voltage induced in the detection coil is a measure for the electrical conductivity of the tissue to be examined and depends on the conductivity and the geometry of the tissue and the geometries of the excitation coil and the detection coil.

Typically, a value of the magnetic excitation field is orders of magnitude higher than a value of the magnetic response field such that the current induced in the detection coil in response to the magnetic response field comprises a low magnitude.

Usually, the excitation coil and the detection coil of the coil arrangement are located close to one another such that the magnetic excitation field may also be present at the location of the detection coil. Accordingly, a current or a voltage may also be induced in the detection coil in response to the magnetic excitation field penetrating through the detection coil. This current or voltage may superimpose the current or voltage induced in response to the magnetic response field, whereby the detection of the magnetic response field by the detection coil may be hampered.

U.S. Pat. No. 7,164,941 B2 describes a method of and an apparatus for determining sleep states of a person. The apparatus utilizes the magnetic induction impedance measurement technique and comprises an excitation coil and first and second detection coils arranged in an axial gradiometer configuration. To this end, the first and second detection coils are electrically connected in series to one another and are arranged parallel to one another. Further, the excitation coil is arranged between the first and second detection coils and is arranged parallel to each of the detection coils. A sleep state of the person to be examined is derived from the voltage induced in the first and second detection coils. Owing to the axial gradiometer configuration, an effect of the magnetic excitation field in the first and second detection coils is cancelled by currents induced in the first and second detections coils adding up to zero. Thus, the measured voltage induced in the detection coil in response to the magnetic response field is indicative of the sleep state of the person.

However, this cancellation of the magnetic excitation field in the detection coil may be highly sensitive to mechanical misalignments of the arrangement of the excitation coil and the first and second detection coils relative to one another. Further, mechanical vibrations of the components of the coil arrangement as well as thermal expansions of the material of the excitation coil and the first and second detection coils may also reduce the cancellation of the effect of the magnetic excitation field at the first and second detection coils. Thus, an accuracy of the determination of the sleep state of the person to be examined may be poor.

SUMMARY OF THE INVENTION

It may be an object of the present invention to provide a coil arrangement for an accurate determination of a physiological parameter of a person. In particular, it may be an object to provide a coil arrangement for a magnetic induction impedance measurement apparatus, which may comprise a high sensitivity for a magnetic response field and meanwhile provide an improved minimization of the magnetic excitation field at the detection coil.

This object defined above is solved by a planar coil arrangement for a magnetic induction impedance measurement apparatus, a magnetic induction impedance measurement apparatus for determining a physiological parameter of a person, and a method of determining a physiological parameter of a person according to the independent claims.

According to an exemplary aspect of the invention, a planar coil arrangement for a magnetic induction impedance measurement apparatus is provided, the planar coil arrangement comprising an excitation coil configured for generating a magnetic excitation field in an object (particularly a person), and a detection coil configured for detecting a magnetic response field generated in response to the magnetic excitation field inducing a current in the object (particularly the person), wherein the detection coil is radially symmetrical shaped with respect to the excitation coil and is arranged relative to the excitation coil such that the magnetic excitation field is minimized in the detection coil.

According to another exemplary aspect of the invention, a magnetic induction impedance measurement apparatus for determining a physiological parameter of a person is provided, the magnetic induction impedance measurement apparatus comprising a planar coil arrangement as described above, and a signal processing unit configured for processing a signal generated by a detection coil of the planar coil arrangement.

A use of a planar coil arrangement as described above for determining a physiological parameter of a person is provided.

According to another exemplary aspect of the invention, a method of determining a physiological parameter of a person is provided, the method comprising generating a magnetic excitation field in the person by an excitation coil, detecting a magnetic response field by a detection coil, wherein the magnetic response field is generated in response to the magnetic excitation field inducing a current in the person, wherein the detection coil is radially symmetrical shaped with respect to the excitation coil and is arranged relative to the excitation coil such that the magnetic excitation field is minimized in the detection coil, and determining the physiological parameter of the person based on the magnetic response field In the context of the present application, the term "planar" coil arrangement may particularly denote a coil configuration in which the components of the coil arrangement (particularly an excitation coil and a detection coil) may (essentially) extend in a common plane or in planes being (approximately) parallel to one another but (closely) spaced from one another. In particular, the term "planar" coil arrangement may not refer to a coil arrangement comprising an excitation coil and two detection coils arranged in an axial gradiometer arrangement.

The term "magnetic field" may particularly denote a magnetic flux density B measured in units of Tesla T and/or a magnetic field intensity H measured in units of Ampere per meter. For ease of reading, the term "magnetic field" may be used in the context of the application to refer to the magnetic flux density and/or the magnetic field intensity.

The term "radial symmetrical shape of the detection coil with respect to the excitation coil" may particularly denote that a shape of the detection coil may be invariant with respect to a rotation around a rotational axis particularly being defined by a center of the excitation coil.

The term "minimizing the magnetic excitation field in the detection coil" may particularly denote that a net field strength of the magnetic excitation field may add or integrate to (almost) zero within the extension of the detection coil particularly when considering a winding orientation of the detection coil. The term "winding orientation" of a coil may particularly denote a winding direction of coil windings with respect to a coil shape.

According to the exemplary aspects of the invention, a magnetic induction impedance measurement apparatus may allow for contactlessly determining a physiological parameter of a person to be examined. The magnetic induction impedance measurement apparatus may utilize a planar coil arrangement comprising an excitation coil and a detection coil which may be arranged in a common plane or in parallel planes being close to one another. The detection coil may comprise a radially symmetrical shape with respect to the excitation coil, in order to account for a magnetic excitation field decreasing with a distance from the excitation coil. Further, the detection coil may be arranged relative to the geometry of the excitation coil. Accordingly, a magnetic excitation field may be minimized, particularly cancelled or extincted, in the detection coil owing to the geometry and the arrangement of the detection coil. Here, the term "geometry" of a coil may particularly denote a shape and/or dimensions of the coil.

Thus, an accuracy of the detection of the magnetic response field by the detection coil may be increased, since the magnetic excitation field may be minimized in the detection coil. Accordingly, the detection coil may be configured for detecting a current induced in the detection coil in response to the magnetic response field which current may not be superimposed by currents induced in the detection coil in response to the magnetic excitation field. Thus, an accuracy of the determination of the physiological parameter of the person may be increased.

In particular, the planar coil arrangement may allow for a mechanically easy configuration of the coil arrangement, in order to reduce effects of mechanical misalignments of the excitation coil and the detection coil relative to one another, mechanical vibrations of the excitation coil and the detection coil and thermal expansions of the material of the excitation coil and the detection coil on the minimization of the magnetic excitation field in the detection coil. Thus, an accuracy of the determination of a physiological parameter of the person may be increased. In particular, the planar coil arrangement may be manufactured in a cost-effective way, since the planar coil arrangement may have a low profile.

In particular, since the coil arrangement may comprise a single detection coil formed in one plane, which may allow for the minimization of the magnetic excitation field in the detection coil, the coil arrangement may comprise a low complexity such that manufacturing costs of the coil arrangement may be low. In particular, the coil arrangement may not need to comprise further detection coils for accomplishing the minimization of the magnetic excitation field in detection coil.

Next, further exemplary embodiments of the planar coil arrangement for a magnetic induction impedance measurement apparatus will be explained. However, these embodiments also apply to the magnetic induction impedance measurement apparatus, the use of the planar coil arrangement, and the method of determining a physiological parameter of a person.

In particular, the excitation coil may comprise one or a plurality of windings.

In particular, the detection coil may comprise one or a plurality of windings.

In particular, the detection coil may be designed in a planar way. The term "planar" detection coil may particularly denote a coil configuration in which the components of the detection coil (particularly coil windings) may (essentially) extend in a common plane or in planes being (approximately) parallel to one another but (closely) spaced from one another.

The detection coil may extend over an angular range ($\alpha$) (of and) along a circumference of the excitation coil such that the detection coil may comprise a spatial directivity for the detection of the magnetic response field. Here, the term "the detection coil may extend over an angular range along the circumference of the excitation coil" may particularly denote that a total extension of the detection coil may be arranged in the angular range of the excitation coil. In particular, terminal connections of the detection coil may be arranged outside of the angular range of the excitation coil.

In particular, the angular range may comprise (about) 120 degrees)(°), particularly (about) 90°, further particularly (about) 60°, further particularly (about) 30°.

In particular, the excitation coil and the detection coil may be concentrically arranged relative to one another around a common center. Accordingly, an extension of the detection coil may be distributed relative to the geometry of the excitation coil in a radially symmetrical way.

The excitation coil may comprise a circular shape and/or the detection coil may comprise an annulus-like shape. Accordingly, the coil arrangement may be manufactured in an easy and cost-effective way, since the shapes of the excitation coil and/or the detection coil may be simple for providing a minimization of the magnetic excitation field in the detection coil. In particular, a circular excitation coil may cause an excitation field having a uniform field strength inside the excitation coil and a radially decreasing field strength of the excitation field outside of the excitation coil.

In particular, the detection coil may be arranged relative to the object (particularly the person) such that the magnetic response field may be maximized in the detection coil. Thus, a sensitivity of the detection coil with respect to the magnetic response field and accordingly the accuracy of the determination of the parameter of the object may be increased.

The detection coil may comprise a radially outer first coil portion and a radially inner second coil portion connected in series to one another, wherein the first and second coil portions may be annulus-like shaped. In particular, the first and second coil portions may be designed in a planar way. Thus, the detection coil may provide high design flexibility for accomplishing a minimization of the magnetic excitation field in the detection coil, since the shapes and dimensions of the first and second coil portions and a relative arrangement of the first and second coil portions to one another may be selected according to requirements for minimizing the magnetic field in the detection coil.

The excitation coil and the detection coil may overlap one another. Accordingly, a coil portion arranged radially inside of the excitation coil may experience a higher density of the magnetic excitation field compared to a coil arranged radially outside of the excitation coil, and field orientations of the magnetic excitation field in the radially outer coil portion and the radially inner coil portion may be opposite to one another. Thus, a minimization of the magnetic excitation field at the detection coil may be accomplished.

The first coil portion may be arranged radially outside of the excitation coil, the second coil portion may be arranged radially inside of the excitation coil, and a winding orientation of the first coil portion may be identical to a winding orientation of the second coil portion. Accordingly, field orientations of the magnetic excitation field penetrating through the first and second coil portions may be opposite to one another, and thus a total field strength of the magnetic excitation field may be minimized in the detection coil.

The first coil portion and the second coil portion may be arranged radially outside (or radially inside) of the excitation coil, and a winding orientation of the first coil portion may be opposite to a winding orientation of the second coil portion. Accordingly, since an orientation of magnetic flux lines of the magnetic excitation field may be identical in the first and second coil portions, a voltage induced in the first coil portion and a voltage induced in the second coil portion may comprise (almost) identical amplitudes but opposite signs, thereby providing a minimization of the magnetic excitation field in the detection coil.

An extension (A1) of the first coil portion may be larger than an extension (A2) of the second coil portion, such that a density of the magnetic excitation field at the second coil portion may be higher compared to a density of the magnetic excitation field at the first coil portion. In particular the term "extension" of a coil may particularly denote an area which may encompassed by coil windings of the coil. Further, in a case of the magnetic response field having a uniform density at the detection coil, an amount of a voltage induced in the first coil portion may be larger than an amount of a voltage induced in the second coil portion, whereby a selective sensitivity of the detection coil for the magnetic response field may be provided.

A distance of (a center or a circumference of) the first coil portion and/or a distance of a (center or a circumference of) the second coil portion from the excitation coil may be dimensioned in accordance with a parameter of the object to be determined, particularly a physiological parameter of the person. Thus, a sensitivity of the first and/or second coil portion for the magnetic response field to be detected may be selectively increased for the particular parameter of the object to be determined such that an accuracy of the determination of the parameter may be increased.

In particular, the first coil portion and/or the second coil portion may be arranged or positioned relative to the object (particularly the person) such that the magnetic response field may be maximized in the detection coil, particularly in the first coil portion. In particular, the first coil portion may be arranged close to the object such that the magnetic response field may be maximized in the first coil portion. In particular, the second coil portion may be arranged at a greater distance from the object compared to the first coil portion such that the magnetic response field may comprise a lower field strength in the second coil portion compared to the field strength in the second coil portion. In particular, the latter arrangement of the first and/or second coil portions relative to the object may account for a uniform field strength of the magnetic response field at the position of the detection coil. Thus, a sensitivity of the first and/or second coil portion for the magnetic response field to be detected may be selectively adjusted such that an accuracy of the determination of the parameter of the object may be increased.

In particular, the extension of the first coil portion, the extension of the second coil portion, the distance of the first coil portion from the excitation coil, and/or the distance of the second coil portion from the excitation coil may be selected in accordance with the (physiological) parameter to be determined. In particular, an extension of the annulus-like shaped first and second coil portions may comprise a radial width. Further, a distance and/or an arrangement between the person to be examined and the coil arrangement may be selected in accordance with the physiological parameter of the person to be determined. To this end, a value of a vital sign sensitivity (VSS) may be optimized when manufacturing the coil arrangement. In particular, the VSS may be defined as a ratio between a voltage caused in the detection coil by a change in the magnetic response field owing to the physiological parameter and a conductivity change in a tissue of the person owing to the physiological parameter.

In particular, in order to detect a lung activity of a person for a determination of a respiratory rate, a diameter of the circular excitation coil may be (about) 5 centimeters (cm), a radial width of the annulus-like shaped first coil portion may be (about) 3 cm, and a radial distance between the excitation coil and the first coil portion may be (about) 4.5 cm. In case of the annulus-like shaped first coil portion being arranged radially inside of the excitation coil, a radial width of the second coil portion may be (about) 1 cm, and a radial distance of the second coil portion from a center of the excitation coil may be (about) 0.1 millimeter (mm). In case of the annulus-like shaped first coil portion being arranged radially outside of the excitation coil, a radial width of the second coil portion may be (about) 1.5 cm, a radial distance of the second coil portion from the excitation coil may be (about) 5 mm.

In particular, in order to detect a heart activity of a person, a diameter of the circular excitation coil may be (about) 5 cm, a radial width of the annulus-like shaped first coil portion may be (about) 3 cm, and a radial distance between the excitation coil and the first coil portion may be (about) 1.5 cm. In case of the annulus-like shaped second coil portion being arranged radially inside of the excitation coil, a radial width of the second coil portion may be (about) 1 cm, and a radial distance of the second coil portion from a center of the excitation coil may be (about) 0.3 mm. In case of the annulus-like shaped second coil portion being arranged radially outside of the excitation coil, a radial width of the second coil portion may be (about) 1 cm, and a radial distance of the second coil portion from the excitation coil may be (about) 5 mm.

The planar coil arrangement may further comprise at least another detection coil configured for detecting the magnetic response field generated in response to the magnetic excitation field inducing the current in the object, wherein at least another detection coil may be radially symmetrical shaped with respect to the excitation coil and may be arranged relative to the excitation coil such that the magnetic excitation field may be minimized in the detection coil. Thus, the coil arrangement may provide for a location dependent detection of the magnetic response field, in order to provide spatially dependent information of the object to be examined.

In particular, the detection coil and the at least another detection coil may be designed in a planar way. The term "planar" detection coils may particularly denote a coil configuration in which the components of the detection coils (particularly coil windings) may (essentially) extend in a common plane or in planes being (approximately) parallel to one another but (closely) spaced from one another.

The coil arrangement may be manufactured on at least one of a (particularly ceramic) substrate, a printed circuit board, a multilayer printed circuit board, a stack of (multilayer) printed circuit boards, a foil and a textile particularly using photolithography techniques, thus the planar coil arrangement being manufactured in a cost-effective and space-saving way as a laminated structure. In particular, the planar coil arrangement may be applied on the foil by printing techniques such that the foil comprises printed coil windings. In particular, the planar coil arrangement may be applied to the textile by printing or sewing techniques such that the textile comprises printed or sewed coil windings.

Next, further exemplary embodiments of the magnetic induction impedance measurement apparatus for determining a physiological parameter of a person will be explained. However, these embodiments also apply to the coil arrangement, the use of a planar coil arrangement, and the method of determining a physiological parameter of a person.

The physiological parameter may comprise at least one of a lung activity, a heart activity, and a brain activity, such that the magnetic induction impedance measurement apparatus may be usable for determining a vital sign of a person particularly for clinic applications or in the automotive industry. In particular, for determining the brain activity, the magnetic induction impedance measurement apparatus may comprise a hemispherical design with the coil arrangement being arranged at a center of the apparatus close to a circumferential line of the apparatus.

BRIEF DESCRIPTION OF THE DRAWINGS

The invention will be described in more detail hereinafter with reference to examples of embodiment, but to which the invention is not limited.

DETAILED DESCRIPTION OF EMBODIMENTS

Figure 1:
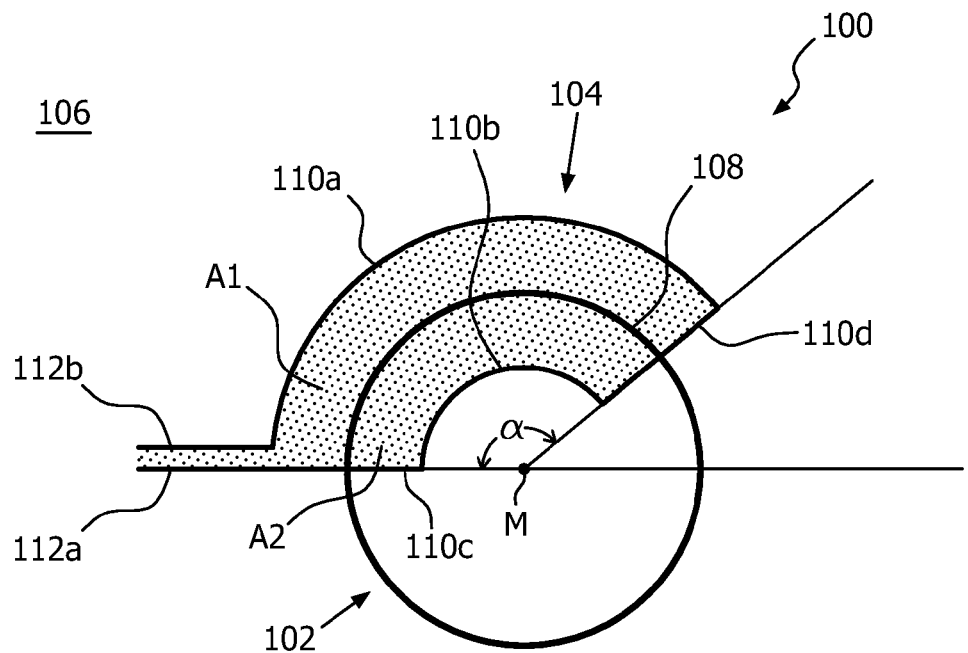
FIG. 1 shows a planar coil arrangement for a magnetic induction impedance measurement apparatus according to a first exemplary embodiment of the invention.

The illustration in the drawing is schematic. It is noted that in different figures, similar or identical elements are provided with the same reference signs or with reference signs, which are different from the respective reference signs only with a first digit.

Referring to FIG. 1, a coil arrangement 100 for a magnetic induction impedance measurement apparatus according to a first exemplary embodiment of the invention will be explained. The coil arrangement 100 comprises an excitation coil 102 and a detection coil 104 arranged in parallel planes. A reference numeral 106 denotes the plane in which the excitation coil 102 extends. The excitation coil 102 and the detection coil 104 are manufactured as laminated copper structures on opposite sides of a printed circuit board using photolithography techniques.

The excitation coil 102 is configured as a circular ring comprising a single winding. Terminal connections of the excitation coil 102 connect the excitation coil 102 to a voltage source configured for providing a time-variable source voltage to the excitation coil 102.

The detection coil 104 comprises a single winding and is annulus-like shaped. The detection coil 104 extends over an angular range α of the excitation coil 104 along a circumference 108 of the excitation coil 102. Further, the excitation coil 102 and the detection coil 104 are concentrically arranged with respect to a center M of the excitation coil 102 such that the detection coil 104 comprises a radially symmetrical shape with respect to the excitation coil 102 within the angular range α.

The detection coil 104 comprises first and second winding portions 110a, b running parallel to the circumference 108 of the excitation coil 102 within the angular range α. Third and fourth winding portions 110c, d of the detection coil 104 extend radial with respect to a geometry of the excitation coil 102. The detection coil 104 overlaps the excitation coil 102 such that an area A1 defined by the first, third and fourth winding portions 110a, c, d of the detection coil 104 is arranged radially outside of the excitation coil 102, and an area A2 defined by the second, third and fourth winding portions 110b, c, d of the detection coil 104 is arranged radially inside of the excitation coil 102. The area A1 is larger than the area A2. Terminal portions 110a, b of the detection coil 104 are connected to the first and second winding portions 110a, b and radially extend with respect to the center M of the excitation coil 102. For illustration purposes, an area encompassed by the detection coil 104 (including the terminal portions 110a, b) is illustrated in a dotted way.

The excitation coil 102 comprises a diameter of 5 cm, and a width of the annulus-like shaped second coil portion 420b measured in a radial direction from the center M is dimensioned to be 35 mm. A radial distance between the center M and the winding portion 110b of the detection coil 104 is 5 mm, and the angle α measures 120°.

For determining a parameter of the object, the object is arrangeable at a distance of 5 cm below a center of the detection coil 104.

In operation of the coil arrangement 100, a magnetic excitation field is generated by a time-variable current fed by the voltage source to the excitation coil 102. The magnetic excitation field comprises flux lines running through the plane 106 in a perpendicular way. A density of the flux lines of the magnetic excitation field within the excitation coil 102 and thus in the area A2 is approximately uniformly distributed, whereas a density of the flux lines of the magnetic excitation field within the area A1 is decreasing with a radial distance from the center M. A sign of the magnetic excitation field at the area A1 is opposite to a sign of the magnetic excitation field at the area A2. Thus, the magnetic excitation field integrates to zero in the detection coil 104. Accordingly, currents induced in the radially outer and radially inner portions of the detection coil 104 in response to the magnetic excitation field comprises opposite signs but a similar amplitude and thus almost cancel one another. The magnetic response field generated by eddy currents in the conductive object to be examined perpendicularly penetrates the area A1 and A2 of the detection coil 104 with a common density and accordingly induces a current in the detection coil 104 to be measured for further processing.

Figure 2:
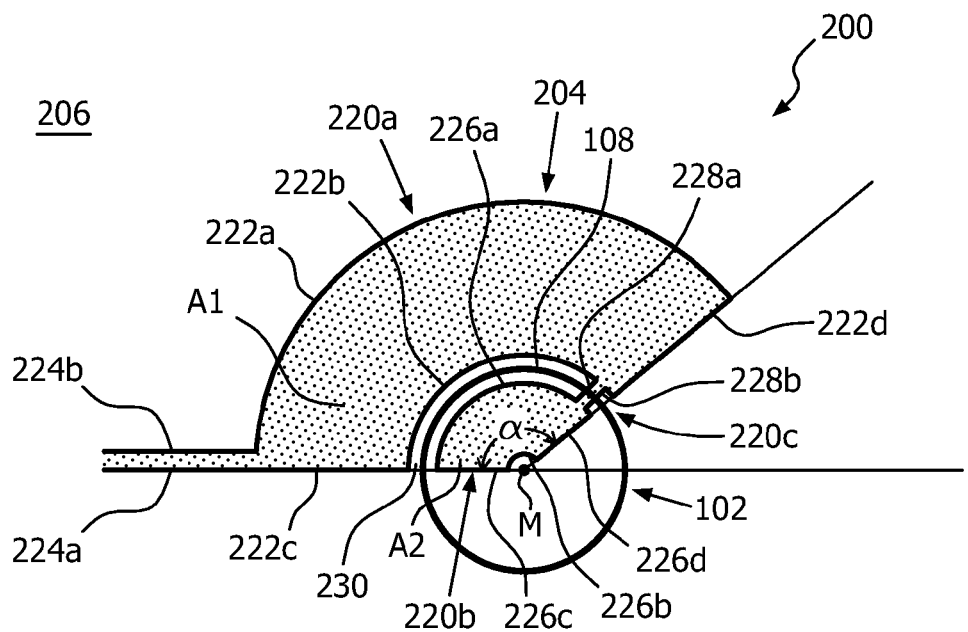
FIG. 2 shows a planar coil arrangement for a magnetic induction impedance measurement apparatus according to a second embodiment of the invention.

Referring to FIG. 2 a coil arrangement 200 for a magnetic induction impedance measurement apparatus according to a second exemplary embodiment of the invention will be explained. Similarly to the coil arrangement 100, the coil arrangement 200 comprises an excitation coil 102 and a detection coil 204 arranged in a common plane 206. The excitation coil 102 and the detection coil 204 are manufactured as laminated copper structures on one side of a ceramic substrate using photolithography techniques.

The coil arrangement 200 comprises an excitation coil 102 which is identical to the excitation coil 102 illustrated in FIG. 1.

Similar to the detection coil 104, the detection coil 204 comprises a single winding and an overall annulus-like shape. The detection coil 204 also extends over an angular range α of the excitation coil 204 along a circumference 108 of the excitation coil 102. Further, the excitation coil 102 and the detection coil 204 are concentrically arranged with respect to the center M such that the detection coil 204 comprises an overall radial symmetrically shape with respect to the center M. The detection coil 204 comprises a first coil portion 220a and a second coil portion 220b being connected to one another in series by a strip-like connecting portion 220c. The first coil portion 220a is arranged radially outside of the excitation coil 102, the second coil portion 220b is arranged radially inside of the excitation coil 102, and the connection portion 220c crosses the excitation coil 102 without contacting the excitation coil 102 in that the connection portion 220c is step-like dislocated from the common plane 206. The connection portion 220c is arranged at an ending portion of the first and second coil portions 220a, b when seen along a circumferential direction of the first and second coil portions 220a, b. Further, winding orientations of the first and second coil portions 220a, b are identical to one another.

The first coil portion 220a comprises an annulus-like shape comprising first and second winding portions 222a, b running parallel to a circumference 108 of the excitation coil 102. Third and fourth winding portions 222c, d extend radially with respect to the center M of the excitation coil 102. Terminal portions 224a, b of the detection coil 204 are connected to the first and second windings 220a, b of the first and second coil portion 220a and extend radially with respect to the center M. The second coil portion 220a comprises first and second winding portions 226a, b running parallel to the circumference 108 of the excitation coil 102. Third and fourth winding portions 226c, d of the second coil portion 220b extend radially with respect to the excitation coil 102. The second winding portion 224b of the first coil portion 220a is connected to the first winding portion 226b of the second coil portion 220b via parallel winding portions 228a, b of the strip-like connection portion 220c of the detection coil 204. An area A1 defined by the first coil portion 220a is larger than an area A2 defined by the second coil portion 220b. An area defined by the connection portion 220c is significantly smaller that the areas A1, A2. Accordingly, the first and second coil portions 220a, b are connected via an annulus-like gap 230 of a small radial width. For illustration purposes, an area encompassed by the detection coil 204 (including the terminal portions 224a, b) is illustrated in a dotted way.

A radial width of the second coil portion 220b is 17 mm, and a radial width of the first coil portion 220a is 30 mm. A radial distance between the excitation coil 102 and the second coil portion 220b is 0.1 mm, and a radial distance between the second coil portion 220b and the first coil portion 220a is 5 mm. The angle α is 120°.

For determining a parameter of the object, the object is arrangeable at a distance of 7 cm below a center of the coil portion 220a of the detection coil 204.

In operation of the coil arrangement 200, a magnetic excitation field is generated by the excitation coil 102. Magnetic flux lines of the magnetic excitation field run vertically with respect to the common plane 206 of the coil arrangement 200. Directions of the magnetic flux lines penetrating through the area A1 and the area A2 are opposite to one another. Accordingly, since a density of the magnetic flux lines through the area A2 is higher than a density of the magnetic flux lines through the area A1 and since the area A1 is larger than the area A2, an effect of the magnetic excitation field in the detection coil 204 is minimized, as described with reference to FIG. 1. Further, a magnetic response field is generated by eddy currents induced in the conductive object to be examined. The magnetic response field penetrates the detection coil 204 with a uniform density of magnetic flux lines. A current is accordingly induced in the first and second coil portions 220a, b of the detection coil in response to the magnetic response field. As the area A1 of the first coil portion 220a is significantly larger than the area A2 of the second coil portion 220b, this induced current is dominated by a current induced in the first coil portion 220a, and a current induced in the second coil portion 220b does not contribute to the total current induced in the detection coil 204 in response to the magnetic response field.

Figure 3:
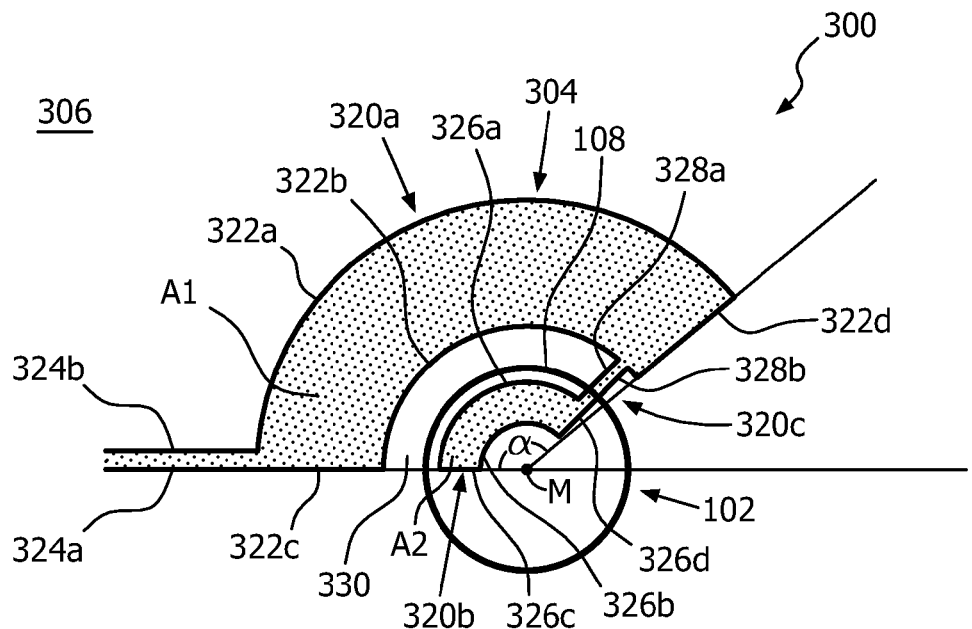
FIG. 3 shows a planar coil arrangement for a magnetic induction impedance measurement apparatus according to a third embodiment of the invention.

Referring to FIG. 3, a coil arrangement 300 for a magnetic induction impedance measurement apparatus according to a third exemplary embodiment of the invention will be explained. The coil arrangement 300 is identical to the coil arrangement 200, however, radial widths of the first and second coil portions 320a, b are smaller than respective radial widths of the first and second coil portions 220a, b. Accordingly, a longitudinal extension of the connection portion 320c measured in a radial direction with respect to the excitation coil 102 is larger than a longitudinal extension of the connection portion 220c.

A radial width of the second coil portion 320b is 5 mm, and a radial width of the first coil portion 320a is 20 mm. A radial distance between the excitation coil 102 and the second coil portion 320b is 5 mm, and a radial distance between the second coil portion 320b and the first coil portion 320a is 10 mm. The angle α measures 120°.

For determining a parameter of the object, the object is arrangeable at a distance of 6 cm below a center of the coil portion 320a of the detection coil 304.

An operation of the coil arrangement 300 is identical to an operation of the coil arrangement 200.

Figure 4:
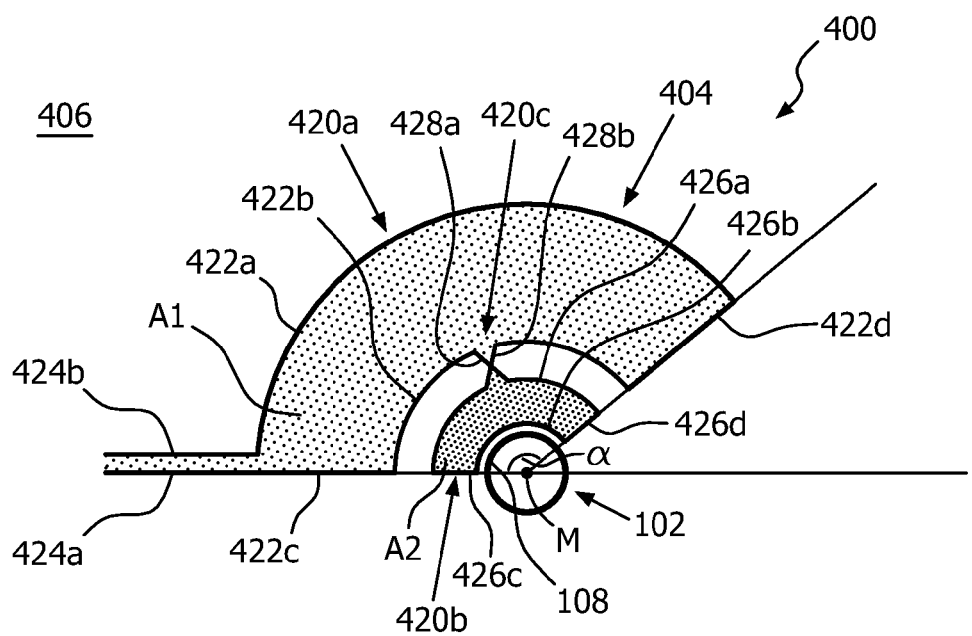
FIG. 4 shows a planar coil arrangement for a magnetic induction impedance measurement apparatus according to a fourth embodiment of the invention.

Referring to FIG. 4, a planar coil arrangement 400 for a magnetic induction impedance measurement apparatus according to a fourth exemplary embodiment of the invention will be explained. The coil arrangement 400 comprises an excitation coil 102 and a detection coil 404 arranged in a common plane 406. The excitation coil 102 and the detection coil 404 are manufactured as laminated copper structures on one side of a textile substrate using lithography techniques.

The excitation coil 102 of the coil arrangement 400 is identical to the excitation coil 102 illustrated in FIGS. 1-3. Similar to the detection coil 204, 304, the annulus-like shaped detection coil 404 is arranged radially outside of the excitation coil 102 and comprises a first annulus-like shaped coil portion 420a, a second annulus-like shaped coil portion 420b, and a connection portion 420c. Further, the connection portion 420c is arranged symmetrically with respect to the annulus-like shape of the detection element 404. First and second winding portions 428a,b of the connection portion 420c cross each other such that the second coil portion 420b comprises an opposite winding orientation compared to the first coil portion 420a. An area A1 defined by the first coil portion 420a is larger than an area A2 defined by the second coil portion 420b. An area defined by the connection portion 420c is significantly smaller that the areas A1, A2. For illustration purposes, an area encompassed by the detection coil 404 (including the terminal portions 424a, b) is illustrated in a dotted way with the area A2 having a higher dot-density compared to the area A1 and the area encompassed by the terminal connections 424a, b.

A radial width of the annulus-like shaped second coil portion 420b is 5 mm, and a radial width of the annulus-like shaped first coil portion 420a is 30 mm. A radial distance between the excitation coil 102 and the second coil portion 420b is 5 mm, and a radial distance between the second coil portion 420b and the first coil portion 420a is 5 mm. The angle α is 120°.

For determining a parameter of the object, the object is arrangeable at a distance of 5 cm below a center of the coil portion 420a of the detection coil 404.

An operation of the coil arrangement is similar to an operation of the coil arrangement 200. However, directions of magnetic flux lines of the magnetic excitation field in the areas A1, A2 are identical to one another owing to the first and second coil portions 420a, b being arranged radially outside of the excitation coil 102. Since the winding orientations of the first and second soil portions 420a, b are opposite to one another, currents induced in the first coil portion 420a and in the second coil portion 420b in response to the magnetic excitation field comprise opposite signs but equal amplitudes. Accordingly, the magnetic excitation field in the detection coil 404 is cancelled. Further, as the densities of the magnetic flux lines of the magnetic response field in the areas A1, A2 of the first and second coil portions 420a,b are identical but the area A1 is larger than the area A2, a total current induced in the detection coil 402 is dominated by a current induced in the first coil portion 420a of the detection coil 402.

Figure 5:
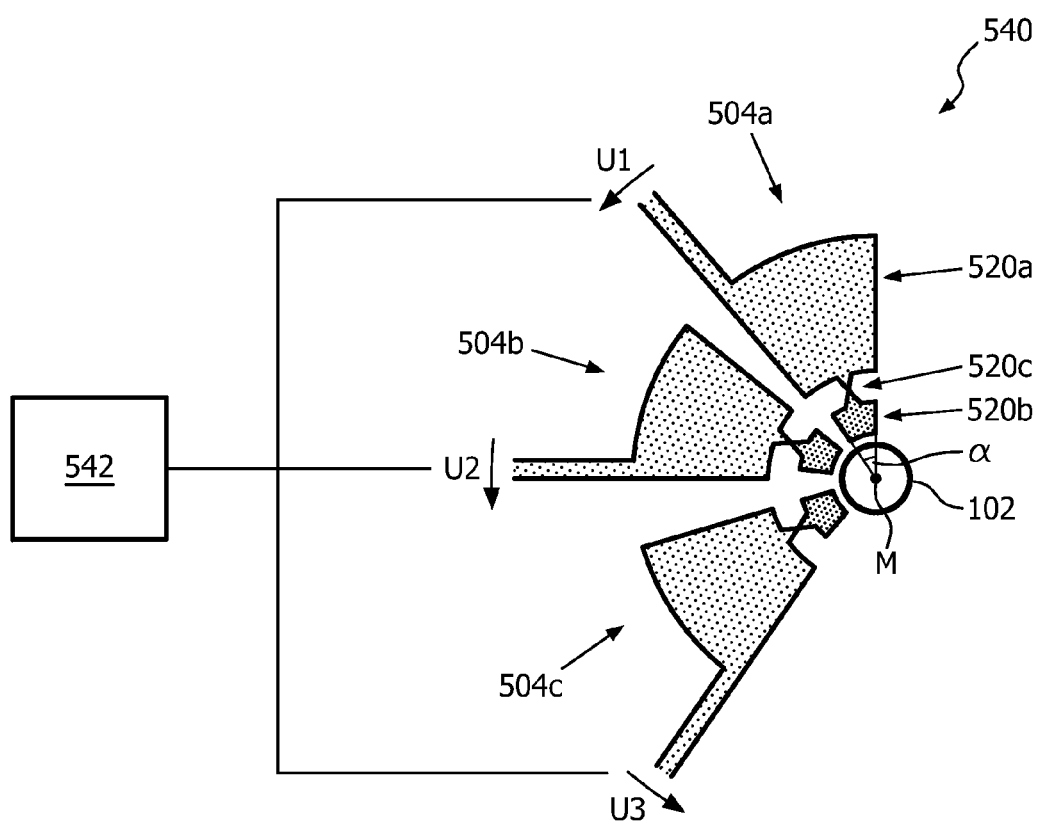
FIG. 5 shows a magnetic induction impedance measurement apparatus according to an exemplary embodiment of the invention.

Referring to FIG. 5, a magnetic induction impedance measurement apparatus 540 for determining a heart activity of a person according to an exemplary embodiment of the invention will be explained. The apparatus 540 comprises a coil arrangement 500 which is designed based on the coil arrangement 400 illustrated in FIG. 4. The coil arrangement 500 comprises an excitation coil 102 identically designed to the excitation coil 102 illustrated in FIG. 4 and three detection coils 504a-c each of which being identically designed as the detection coil 402. However, the angular range a of the detection coils 504a-c measures 50° instead of 120° as illustrated in FIG. 4. The first, second and third detection coils 504a-c are arranged adjacent to one another when seen along a circumferential direction of the excitation coil 502. For sake of clarity, reference numerals are only assigned to the detection coil 504a.

The dimensions and the relative arrangement of the excitation coil 102 and the detection coils 504a-c are selected in accordance with maximizing the magnetic response field in the detection coils 504a-c for the determination of the heart activity of the person in terms of providing a signal to be measured which is dominated by the signal derived from the first coil portions 520a.

Further, the magnetic induction impedance measurement apparatus 540 comprises a signal processing unit 542 configured for determining the heart activity of the person based on measured voltages induced in the detection coils 504a-c in response to the magnetic response field.

In operation of the magnetic induction impedance measurement apparatus 540, the person to be examined is placed at a distance of 5 cm below the coil arrangement 500 with a body region comprising the heart being located under first coil portions 502a of the detection coils 504a-c. Voltages U1-U3 extracted from the detection coils 504a-c are measured by the signal processing unit 542. Further, the signal processing unit 542 generates a spatial-dependent picture of the heart region of the person based on the voltage signals U1-U3 for determining the heart activity of the person.

Alternatively, the detection coils 504a-c may be designed differently with respect to one another, and the first detection coil 504a may be designed and arranged relative to the excitation coil 102 similarly to the detection coil 104, the second detection coil 504b may be designed and arranged relative to the excitation coil 102 similarly to the detection coil 204, and the third detection coil 504a may be designed and arranged relative to the excitation coil 102 similarly to the detection coil 304.

Further, in order to detect the lung activity of the person for a determination of the respiratory rate, a radial distance between the excitation coil 102 and the second coil portion 520b is 5 mm, and a radial distance between the second coil portion 520b and the first coil portion 420b is 30 mm. Radial widths of the first and second coil portions 520a, b are 5 mm and 30 mm, respectively. Alternatively, the distance between the center M and the second coil portion 520a is 1 mm, i.e. the second coil portion is arranged radially inside of the excitation coil 102. In this case, the radial width of the second coil portion 520b is about 2 mm.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the use of the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A planar coil arrangement for a magnetic induction impedance measurement apparatus, the planar coil arrangement comprising:
   an excitation coil configured for generating a magnetic excitation field in an object, and
   a detection coil configured for detecting a magnetic response field generated in response to the magnetic excitation field inducing a current in the object, wherein the excitation coil and the detection coil are concentrically arranged relative to one another around a common center; the windings of the detection coil are arranged relative to the excitation coil such that currents induced in response to the magnetic excitation field comprise opposite signs, but similar amplitudes.

2. The planar coil arrangement according to claim 1, wherein the detection coil extends over an angular range (α) along a circumference of the excitation coil.

3. The planar coil arrangement according to claim 1, wherein the excitation coil comprises a circular shape and/or wherein the detection coil comprises an annulus-like shape.

4. The planar coil arrangement according to claim 1, wherein the detection coil comprises a radially outer first coil portion and a radially inner second coil portion connected in series to one another, wherein the first and second coil portions are annulus-like shaped.

5. The planar coil arrangement according to claim 1, wherein the excitation coil and the detection coil overlap one another.

6. The planar coil arrangement according to claim 4, wherein the first coil portion is arranged radially outside of the excitation coil, wherein the second coil portion is arranged radially inside of the excitation coil, and wherein a winding orientation of the first coil portion is identical to a winding orientation of the second coil portion.

7. The planar coil arrangement according to claim 4, wherein the first coil portion and the second coil portion are arranged radially outside of the excitation coil, and wherein a winding orientation of the first coil portion is opposite to a winding orientation of the second coil portion.

8. The planar coil arrangement according to claim 4, wherein an extension (A1) of the first coil portion is larger than an extension (A2) of the second coil portion.

9. The planar coil arrangement according to claim 4, wherein a distance of the first coil portion and/or a distance of the second coil portion from the excitation coil are dimensioned in accordance with a parameter of the object to be determined.

10. The planar coil arrangement according to claim 1, the planar coil arrangement further comprising:
   at least another detection coil configured for detecting the magnetic response field generated in response to the magnetic excitation field inducing the current in the object, wherein the at least another detection coil is radially symmetrical shaped with respect to the excitation coil and is arranged relative to the excitation coil such that the magnetic excitation field is minimized in the detection coil.

11. The planar coil arrangement according to claim 1, wherein the planar coil arrangement is manufactured on at least one of a substrate, a printed circuit board, a multilayer printed circuit board, a foil, and a textile.

12. A magnetic induction impedance measurement apparatus for determining a physiological parameter of a person, the magnetic induction impedance measurement apparatus comprising:
   a planar coil arrangement according to claim 1, and
   a signal processing unit configured for processing a signal generated by a detection coil of the planar coil arrangement.

13. The magnetic induction impedance measurement apparatus according to claim 12, wherein the physiological parameter comprises at least one of a lung activity, a heart activity, and a brain activity.

14. A method for magnetic induction impedance measurement, the method comprising:
   generating a magnetic excitation field in a person by an excitation coil,
   detecting a magnetic response field by a detection coil, wherein the magnetic response field is generated in response to the magnetic excitation field inducing a current in the person, wherein the excitation coil and the detection coil are concentrically arranged relative to one another around a common center; the windings of the detection coil are arranged relative to the excitation coil such that currents induced in response to the magnetic excitation field comprise opposite signs, but similar amplitudes, and
   determining a physiological parameter of the person based on the detected magnetic response field.

* * * * *